United States Patent

Buzerak et al.

[11] Patent Number: 5,356,424
[45] Date of Patent: Oct. 18, 1994

[54] LAPAROSCOPIC SUTURING DEVICE

[75] Inventors: John E. Buzerak, Poughquag, N.Y.;
Robert J. Bedard, Southbury, Conn.;
Janniah S. Prasad, Norwalk, Conn.;
Charles L. Putnam, Fairfield, Conn.;
Lester Miller, Danbury, Conn.;
Steven I. Becker, Bergen, N.J.; James
Coleman, Richmond, England

[73] Assignee: American Cyanamid Co., Wayne, N.J.

[21] Appl. No.: 13,871

[22] Filed: Feb. 5, 1993

[51] Int. Cl.⁵ .............................................. A61B 17/00
[52] U.S. Cl. ........................... 606/223; 606/147; 112/169; 112/80.03
[58] Field of Search .......... 606/139, 144, 147, 148, 606/222-227; 223/102; 163/5; 112/80.03, 169; 81/3.45

[56] References Cited

U.S. PATENT DOCUMENTS

| 67,545 | 8/1867 | Hodgins | 606/222 |
| 196,226 | 10/1877 | Havell | 81/3.45 |
| 242,602 | 6/1881 | Clough | 81/3.45 |
| 4,204,541 | 5/1980 | Kapitanov | 606/145 |
| 4,641,652 | 2/1987 | Hutterer et al. | 606/148 |
| 4,969,892 | 11/1990 | Burton et al. | 606/148 |
| 5,041,127 | 10/1991 | Troutman | 606/223 |
| 5,053,047 | 10/1991 | Yoon | 606/223 |
| 5,152,769 | 10/1992 | Baber | 606/145 |

FOREIGN PATENT DOCUMENTS

| 4114204 | 11/1992 | Fed. Rep. of Germany | 606/148 |
| 0923530 | 5/1982 | U.S.S.R. | 606/148 |
| 1034728 | 8/1983 | U.S.S.R. | 606/224 |
| 1331495 | 8/1987 | U.S.S.R. | 606/222 |

Primary Examiner—Stephen C. Pellagrino
Assistant Examiner—Jeffrey A. Schmidt
Attorney, Agent, or Firm—Charles F. Costello, Jr.

[57] ABSTRACT

A laparoscopic suturing device includes a suturing needle and a driver for manipulating the needle. The suturing needle features a helically-wound front-end portion with a needle point at its proximal end for penetrating tissue and a rear-end portion connected to the driver. The slender design of the suturing device is ideally suited for minimally-invasive surgery.

6 Claims, 7 Drawing Sheets

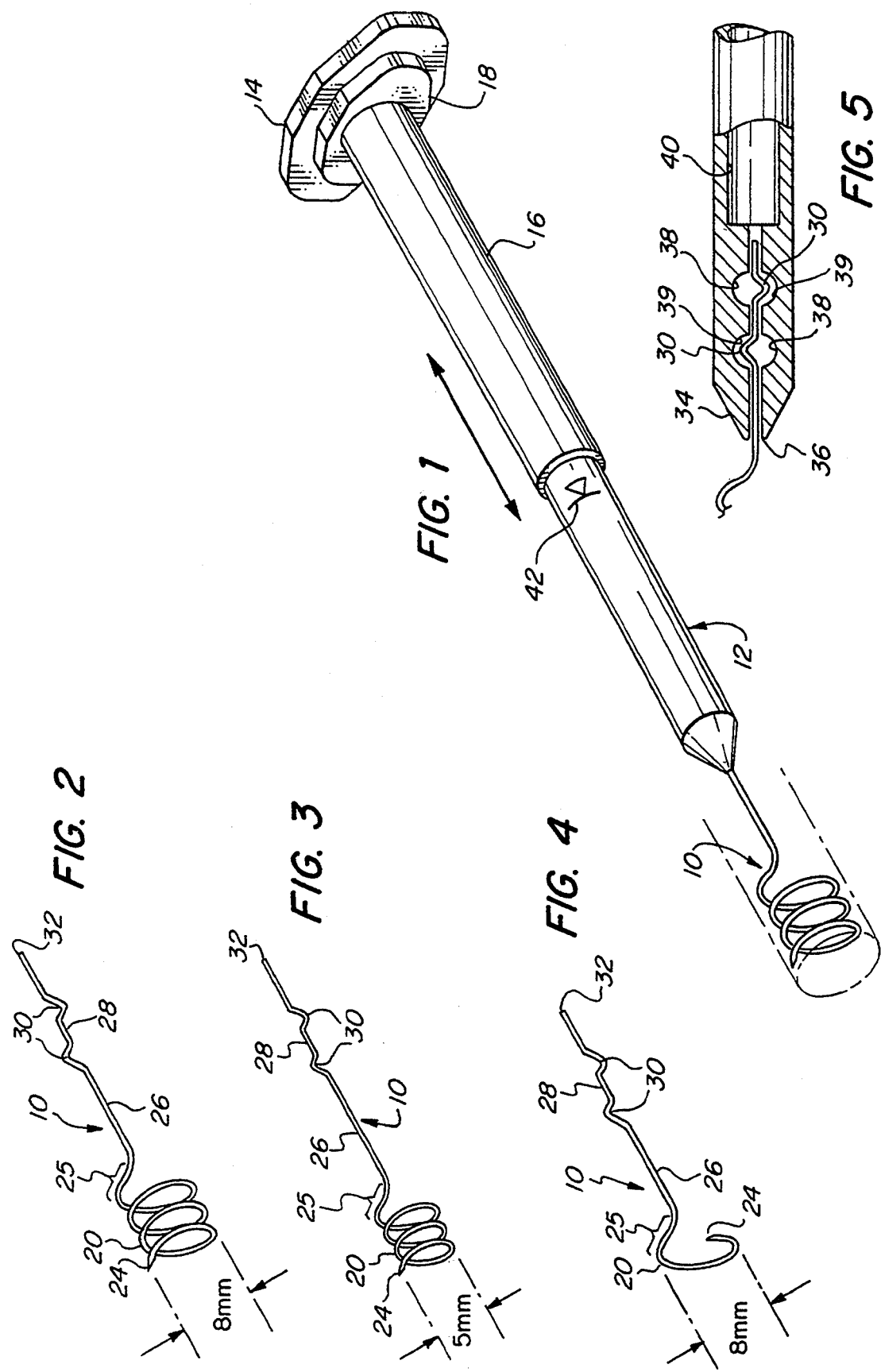

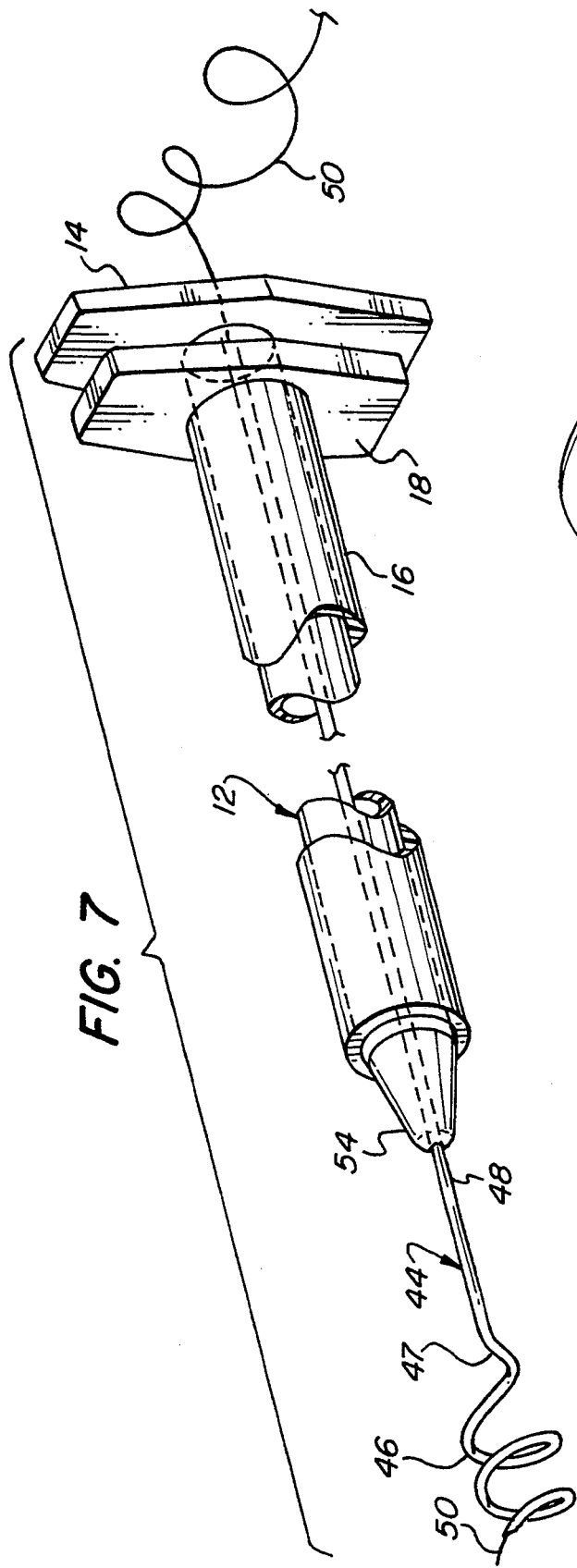
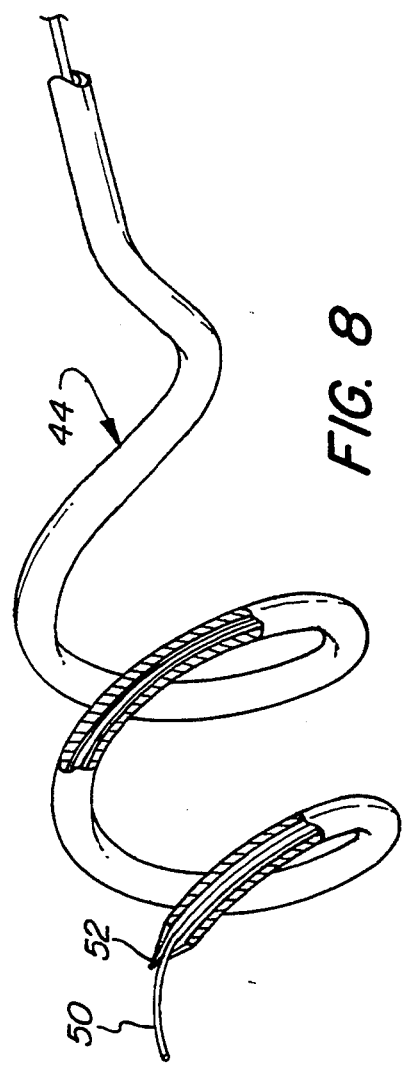
FIG. 7
FIG. 8

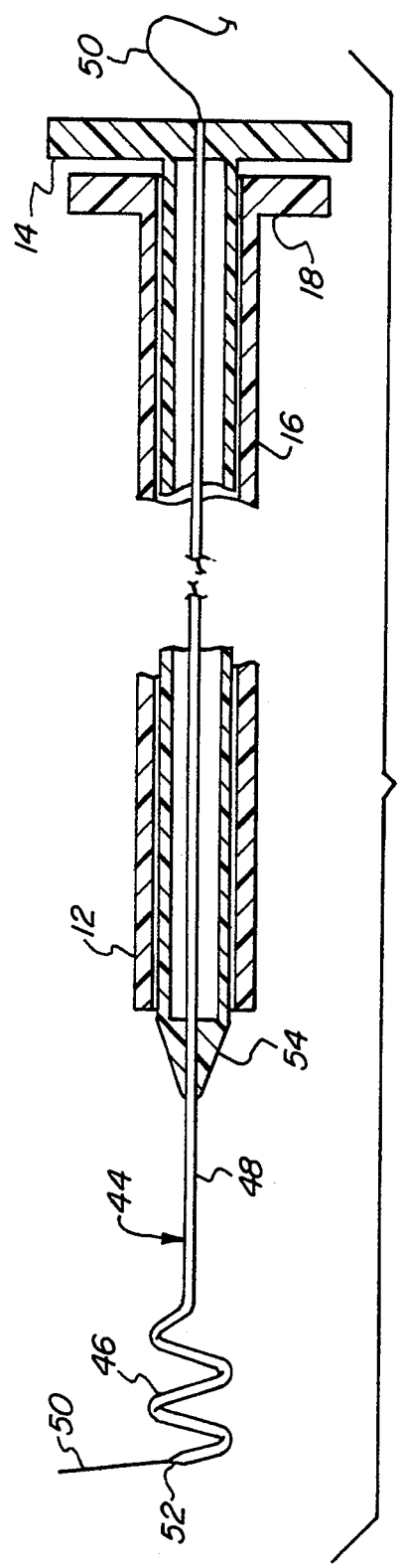
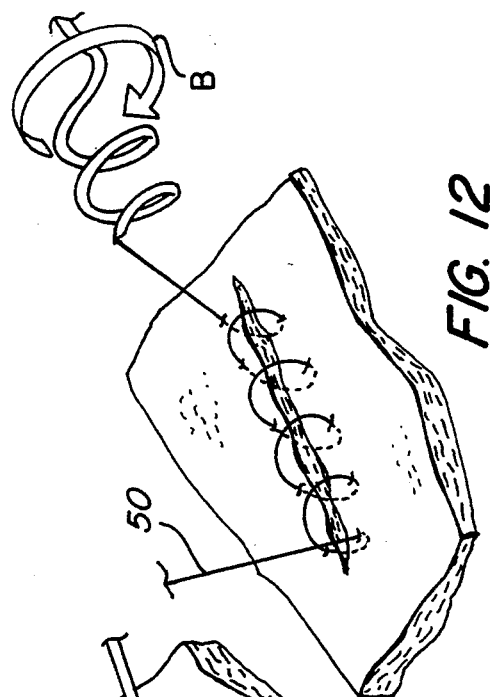
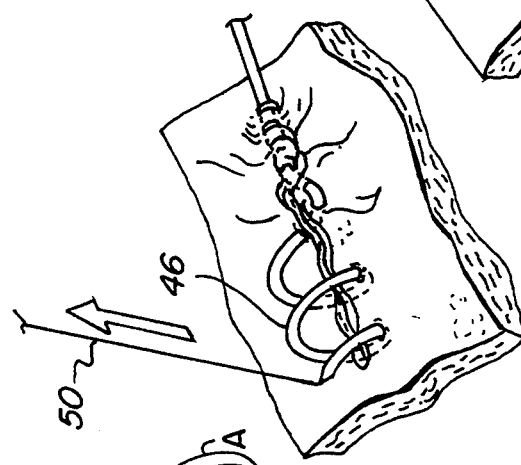
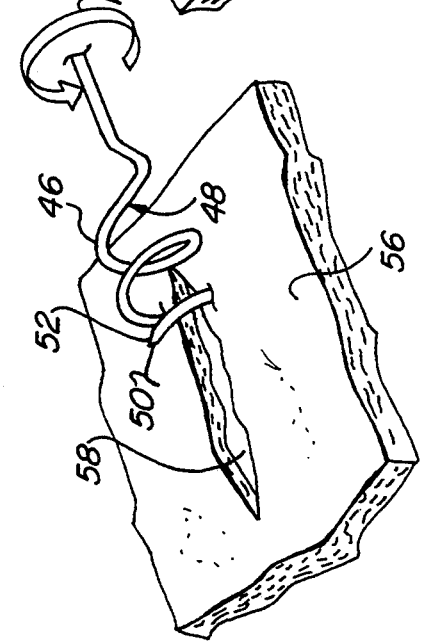
FIG. 9
FIG. 10
FIG. 11
FIG. 12

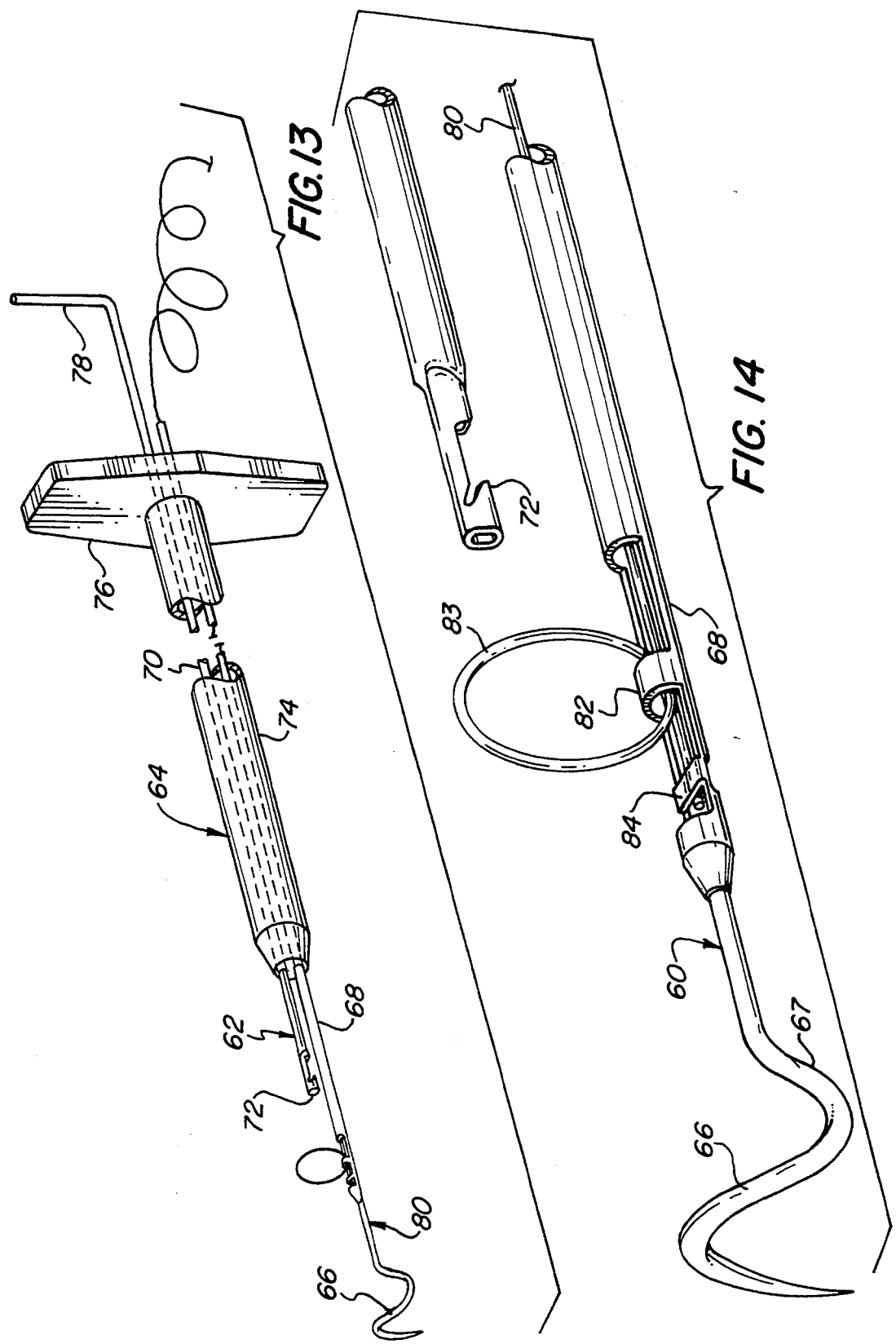

LAPAROSCOPIC SUTURING DEVICE

BACKGROUND OF THE INVENTION

1. Field of the Invention

The present invention relates generally to a medical suturing device ideally suited for use in minimally-invasive surgery, and more particularly to a laparoscopic suturing device for suturing incisions during laparoscopic surgery.

2. Description of the Prior Art

The increasingly popular practice of minimally-invasive, or non-invasive, surgery utilizes medical instruments inserted through one or more cannulas in a patient's body and manipulated from outside of the body by a surgeon. The well-known benefits of using minimally-invasive surgery stem from the need to make only one or more relatively small puncture wounds in a patient and include a reduced risk of infection and faster recovery time.

In one example, intestinal surgery can be performed by inserting laparoscopic surgical instruments through cannulas placed in puncture wounds in the patient's abdominal wall. To conclude the surgery, a laparoscopic suturing device must be used to close the incisions inside the abdominal chamber.

One known suturing device for use in minimally invasive surgery is disclosed in U.S. Pat. No. 5,152,769 (Baber). In that patent, an arcuate needle is secured to a barrel and fed with one end of a suturing thread. The suturing thread extends through a bore in the needle and emerges through an opening proximal to the needle tip. A knot is tied at the end of the suturing thread so when the needle punctures a hole in the tissue, the knot will not be able to follow the needle tip through the hole in the tissue. An arc, or loop, of suturing thread is formed when the needle tip extends through the tissue and the suturing thread is pulled through the bore as the knot remains outside of the hole. The loop is then captured and held by a separate member. The needle tip is backed out of the hole in the tissue and threaded through the loop to form a chain stitch.

While the apparatus described in the Baber patent may have certain benefits, further improvements in laparoscopic suturing devices are desirable to simplify the process of suturing incisions, increase the speed and precision at which such sutures are made, and otherwise generally overcome shortcomings with conventional suturing devices.

SUMMARY OF THE INVENTION

Accordingly, it is a general object of the present invention to provide an improved laparoscopic suturing device.

It is another object of the invention to provide a novel and uniquely shaped suturing needle for performing laparoscopic surgery.

It is a further object of the invention to provide a suturing device wherein the suturing thread can be easily withdrawn from the body after suturing the tissue.

It is another object of the invention to provide a suturing device with a driving assembly for easily, yet effectively, manipulating the suturing needle.

It is still another object of the invention to provide a suturing device that can protect the patient's body from the suturing needle as it is inserted through a cannula.

In accordance with a general aspect of the invention, a laparoscopic suturing device comprises a suturing needle formed with a helically-wound front-end portion having a sharp needle point at its distal end for penetrating tissue; a curved transition portion; and a rear-end portion axially aligned with the front-end portion; and a driver connected to the rear-end portion for manipulating the suturing needle.

The suturing needle is preferably helically-wound with at least a segment of one turn. The needle point continuously punctures the tissue as it travels therethrough in a corkscrew-like manner by rotating the helix about its axial center.

In accordance with another aspect of the invention, a laparoscopic suturing device comprises a suturing needle formed with a helically-wound front-end portion having a sharp point at its distal end for penetrating tissue, a rear-end portion, a substantially straight middle portion connected to the rear-end portion, and a transitional portion connected between the middle portion and the helically-wound front-end portion, with the middle portion being axially aligned with the front-end portion; and a driver connected to the rear-end portion.

In this preferred embodiment, the suturing needle is detachably connected to the driver so it can be separated therefrom and withdrawn through a cannula after completing the stitching of the tissue.

In accordance with still another aspect of the invention, a laparoscopic suturing device comprises a hollow suturing needle formed with a helically-wound front-end portion having a sharp needle point at its distal end for penetrating tissue, a transitional portion and a rear-end portion axially aligned with the helically-wound front-end portion, the hollow suturing needle housing a length of suturing thread; and a driver assembly comprising a driver, connected at its distal end to the rear-end portion of the suturing needle, and a sleeve insertable through a cannula for housing the suturing needle and the driver.

In this preferred embodiment, the hollow needle housing the suturing thread travels through the tissue in a corkscrew-like manner, carrying the end of the suturing thread at its needle tip. When the needle tip is at the end of the incision, the suturing thread is grasped and the suturing needle is withdrawn from the tissue and removed from the cannula.

In accordance with yet another aspect of the invention, a laparoscopic suturing device comprises a suturing needle formed with a helically-wound front-end portion having a sharp needle point at its distal end for penetrating tissue, a transitional portion and an extended hollow rear-end portion axially aligned with the front-end portion and housing a length of suturing thread and having securing means for securing one end of a suturing thread; an elongated suturing thread retriever having means at its distal end for retrieving the suturing thread; and an elongated housing for housing the suturing needle and the suturing thread retriever. The housing is insertable through a cannula and includes a flange at its proximate end for limiting its axial movement within the cannula.

In this preferred embodiment, the suturing retriever grasps a loop of the suturing thread and withdraws it through the cannula. Then the suturing needle is withdrawn from the tissue and removed through the same cannula.

In accordance with yet another aspect of the invention, a laparoscopic suturing device comprises a suturing needle formed with a helically-wound front-end portion having a sharp needle point at its distal end for penetrating tissue, a transitional portion and an extended hollow rear-end portion axially aligned with the front-end portion and housing a length of suturing thread and having securing means for securing one end of the suturing thread; and an elongated housing for housing the suturing needle. The rear-end portion features a frangible section between the securing means and its proximal end. The housing is insertable through a cannula and has a flange at its proximate end for limiting axial movement within the cannula.

In this preferred embodiment, the front-end portion of the suturing needle and the rear-end portion securing the suturing thread are snapped apart at the frangible section after passing through the tissue and then withdrawn through the cannula.

In accordance with still another aspect of the invention, a suturing needle comprises a helically-wound front-end portion formed with a sharp needle point for puncturing tissue, a rear-end portion defining an axial center of the suturing needle, and means for securing a suturing thread to the suturing needle.

In this preferred embodiment, the helically-wound front end portion can be driven through the tissue in a corkscrew-like manner by rotating the rear-end portion about its axial center. The suturing thread secured to the suturing needle is threaded through the tissue as the front end portion is fed through the tissue.

Thus it will be understood from the summary provided above and the detailed description below that the present invention provides novel means for easily applying sutures in different minimally-invasive surgical procedures.

These and other objects, aspects, features and advantages of the present invention will become apparent from the following detailed description of the preferred embodiments taken in conjunction with the accompanying drawings.

BRIEF DESCRIPTION OF THE DRAWINGS

FIG. 1 is a perspective view of a laparoscopic suturing device in accordance with a first embodiment of the present invention;

FIG. 2 through 4 are perspective views of three alternative suturing needles used in the laparoscopic suturing device of the first embodiment of the present invention;

FIG. 5 is a vertical cross-sectional view of a distal end of a driver of the laparoscopic suturing device shown in FIG. 1;

FIGS. 7 is a perspective view of a laparoscopic suturing device in accordance with a second embodiment of the present invention;

FIG. 8 is an enlarged perspective view of a suturing needle used in the laparoscopic suturing device of the second embodiment of the present invention;

FIG. 9 is a vertical cross-sectional view of the laparoscopic suturing device of that second embodiment;

FIGS. 10 through 12 show one example of an application using the laparoscopic suturing device of the second embodiment;

FIG. 13 is a perspective view of a laparoscopic suturing device in accordance with a third embodiment of the present invention;

FIG. 14 is a perspective view of a suturing needle and a suturing thread retriever used in the laparoscopic suturing device of that third embodiment;

DESCRIPTION OF THE PREFERRED EMBODIMENTS

Figure 6B:
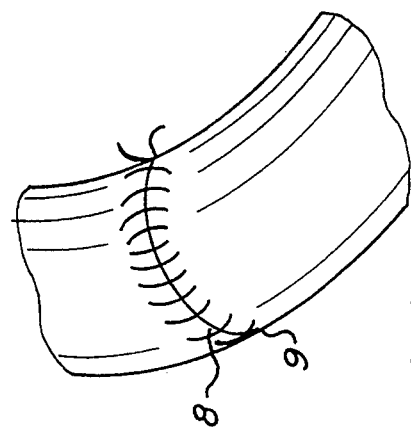
FIGS. 6(a) through 6(d) show one example of an application using the laparoscopic suturing device of the first embodiment.

For ease of reference, as used herein the term "distal" will refer to that part of the suturing device which is farthest from the surgeon-user, and the term "proximal" refers to that part of the suturing device which is closest to the surgeon-user.

A laparoscopic suturing device in accordance with a first embodiment of the present invention is illustrated in FIGS. 1 through 5. The laparoscopic suturing device is shown in FIG. 1 to comprise a suturing needle 10 attached at its proximal end to a driver 12. The driver includes a handle 14, or similar type of gripping means, at its proximal end for manipulating the suturing needle. The driver 12 is a slender elongated shaft, preferably cylindrical in shape, and slides axially within a protective sleeve 16.

As will be appreciated, the suturing device of the present invention is intended, although not limited, to be used in minimally-invasive surgical procedures, and for that purpose that sleeve 16 is designed to fit within a cannula of, for example, 12 mm, communicating from the exterior to the interior of the patient's body. The proximal end of the sleeve 16 is provided with a flange 18 to limit its axial movement within the cannula. Thus, the handle 14 may be operated outside of the patient's body to manipulate the surgical needle 10. When the suturing device is inserted through the cannula and into the body, the driver 12 and the suturing needle 10 can be retracted within the protective sleeve 16.

The suturing needle 10 is shown in detail in FIGS. 2 through 4. That needle is comprised of a helically-coiled front-end portion 20 having a sharp needle tip 24 at its distal end for puncturing the tissue to be sutured, a substantially straight middle portion 26 and a rear-end portion 28. A transitional portion 25 joins the proximal end of the helically coiled front-end portion with the distal end of the middle portion 26. As will be appreciated, the transitional section 25 is curved to align the middle portion with the axial center of the helically coiled front-end portion. The radius of curvature of the transitional portion may be different from that of the helically coiled front-end section. The rear-end portion 28 features an offset region comprised of, for example, two bends 30, or similar wave-like sections offset from the axial center, to be secured in the distal end of the driver 12 as will be described below. The two bends need not necessarily be in the same plane. The dimension of the offset of the bends is shown in enlarged form for clarity. An axial opening 32 is provided in the proximal end of the rear-end portion to receive one end of a suturing thread which is secured therein. Alternatively, a channel in the rear-end portion 28 could be provided instead of the axial opening to secure the suturing thread to the rear-end portion of the needle.

The novel shape of the helically-wound front-end portion 20 enables stitches to be easily placed in the tissue. While the description of FIGS. 2 through 4 is directed to the suturing device of the first embodiment, the following description of the helically-wound front-end portion applies equally to all embodiments of the present invention, which are described below. By simply rotating the suturing needle 10 about its axial center, the front-end portion will rotate in a corkscrew-like manner and the needle tip will be able to continuously puncture the tissue and advance along a suturing path as tissue gathers on the suturing needle. The suturing needle, which can be made of, for example, surgical grade stainless steel, can be sized according to its necessary application. For example, the outside diameter defined by the circumference of the front-end portion, the number of turns and the pitch between each turn can be selected based on the size of incision to be stitched. The suturing needles 10 shown in FIGS. 2 and 3 both have helically-wound front-end portions with 3 turns, but differ in the outside diameter defined by their respective front-end portions. On the other hand, the suturing needle 10 shown in FIG. 4 has the same outside diameter (that is, 8 mm) as the surgical needle shown in FIG. 2, but uses only a segment of one turn. As will be understood, each turn comprises substantially one 360° revolution of the front end portion 20.

The suturing needle 10 is detachably secured to the driver 12 as shown in FIG. 5. More particularly, the driver has a conically-shaped nose portion 34 formed with a slot or bore 36 for receiving therein the rear-end portion 28 of the needle. Within the distal end of the driver 12 are two cavities 38 for receiving the offset sections of the rear-end portion 28. These cavities have side walls 39 that provide comfortably tight lateral support of the offset sections so that any twisting, or torsional force, applied by the driver is transferred to the front-end portion 20 of the suturing needle 10. Likewise, axial movement of the driver is transferred to the suturing needle 10 by virtue of the offset sections being out of alignment with the axial center of the suturing needle and the axis of the slot 36 such that the offset sections are captured in the cavities. It will be understood that the bends 30 forming the offset sections can extend either in the same plane or in different planes from each other, and that the bends or the material of driver 12 can be sufficiently resilient to permit the needle to be urged into and out of the slot 36 for attachment and separation of the two.

An internal bore 40 within the driver stores a desired length of suturing thread and allows it to be dispensed as needed during the suturing procedure. A visual alignment mark 42 is also provided on the exterior of the driver to indicate its axial relationship to the protective sleeve 16.

In use, the suturing device is inserted through a first cannula in the patient's body and the handle 14 is manipulated from outside of the first cannula to axially rotate the driver and drive the suturing needle through the tissue in a corkscrew-like manner. When the last turn of the front-end portion 20 (that is, the turn closest to the middle portion 26) has travelled through the tissue and the front-end portion has completely exited the tissue, the tissue is gathered on the middle portion by, for example, forceps manipulated through a second cannula in the patient's body. The surgical needle 10 is then detached from the driver 12, with an axial detaching force applied by the forceps, and pulled to remove the remaining portion of the surgical needle from the tissue, thereby drawing the thread through the needle punctures. The driver and protective sleeve are withdrawn through the first cannula, as the driver dispenses the suturing thread. The detached surgical needle is then withdrawn through the same cannula and the ends of the suturing thread are cut and knotted to complete the suture.

Figure 6A:
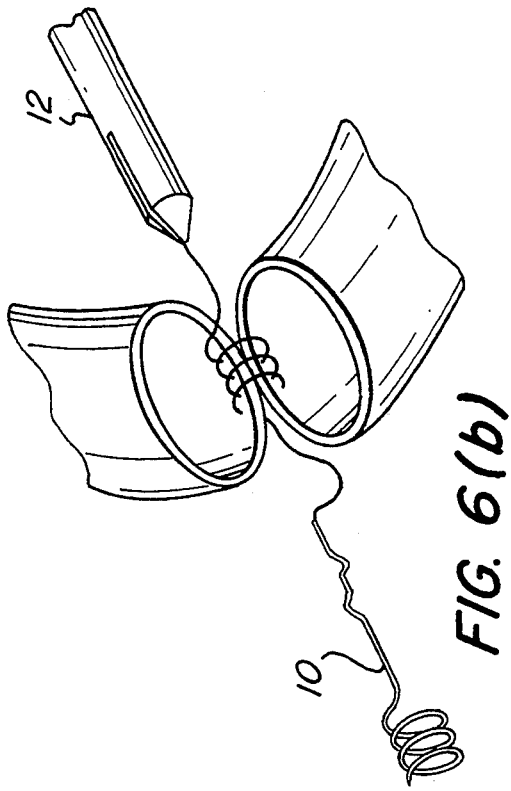
Figure 6D:
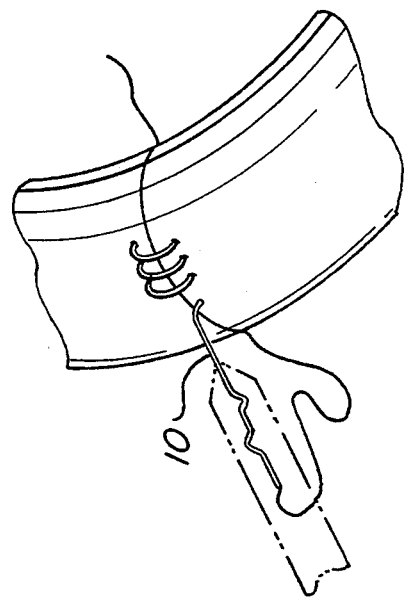
Figure 6C:
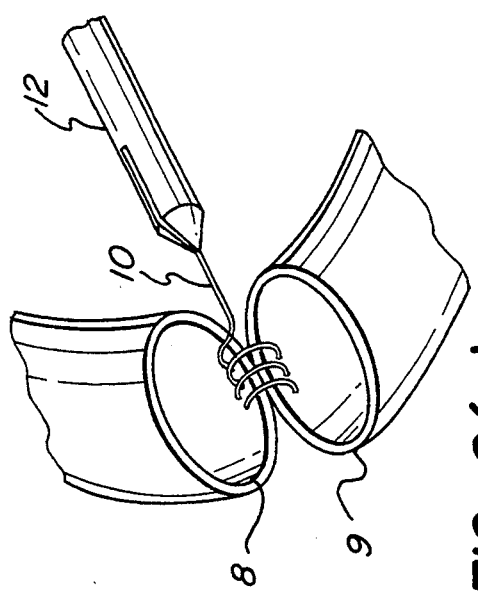

One specific application of the suturing device is shown in FIGS. 6(a) through 6(d). The application shown in these figures is directed to a bowel anastomosis procedure wherein two open ends of a bowel section are joined together. As shown in FIG. 6(a), a first series of stitches is placed in the open ends 8 and 9 of the bowel section by starting from one edge of one of the open ends and driving the suturing needle in a corkscrew-like manner through both edges of the tissue. As shown in FIG. 6(a), it is preferred, but not necessary, to start from the inside edge of one of the open ends because of the way the open ends abut each other. In the manner described above, the front-end portion of the needle exits the tissue after travelling through both open ends one or more times. For example, the first series of stitches can traverse up to 50% of the circumference of the open ends. The punctured tissue is gathered on the middle section by forceps and the surgical needle is withdrawn from the driver as shown in FIG. 6(b). The driver is then withdrawn through a first cannula and re-inserted into the body through another cannula so as to position the driver on the unsutured side of the open ends. As will be appreciated, the suturing thread is dispensed from the driver as it is withdrawn from the first cannula and then cut, leaving enough length for the remaining stitches and to allow the cut end of the thread to remain outside of the first cannula. The suturing needle is re-inserted into the driver and a second series of stitches is placed in the open ends as shown in FIG. 6(c) until the entire circumference is stitched. At that point, the suturing needle is removed from the driver and withdrawn through the first cannula, where the thread is cut, pulled taut and knotted with the loose end of the thread extending from the first cannula. Of course, more than two series of stitches can be used to close the open ends of the bowel section, depending on the preference of the surgeon-user.

The second embodiment of the laparoscopic suturing device shown in FIGS. 7 through 12 is similar to the first embodiment disclosed above in that it provides a driver 12 and handle 14 slidably disposed with a sleeve 16. The sleeve also features a flange 18 at its proximal end. However, a suturing needle 44 in accordance with the second embodiment is hollow throughout its entire length and preferably extends through the entire length of the driver. The suturing needle 44 is comprised of a helically-coiled front-end portion 46, a transitional portion 78 and an extended rear-end portion 48. A suturing thread 50 extends through the suturing needle and protrudes through a sharp needle point 52 at the front-end portion 46 as shown in FIG. 8. The suturing needle 44 is preferably anchored to the driver 12 at a front nose portion 54 and at the handle 14 as best seen in FIG. 9, and is manipulated by operation of the handle.

FIGS. 10 through 12 show one example of using the laparoscopic suturing device of the second embodiment to close an incision 58 in tissue 56. As illustrated, the helically-wound front-end portion 46 can be driven through the tissue 56 on either side of the incision 58 by axially rotating the suturing needle 44 in the direction of arrow A. When the needle point 52 is clear of the incision, the distal end of the suturing thread 50 is grabbed by, for example, forceps operated through a second cannula, and a small length of thread is pulled through the surgical needle. Axial rotation in the direction of arrow B, that is in a direction opposite that of arrow A, is imparted to the suturing needle to back it out of the punctured tissue as the suturing thread is held by the forceps. The entire suturing device is then withdrawn through the cannula. The distal end of the suturing thread is then withdrawn through the same cannula and the ends of the suturing thread are cut and knotted to complete the suture.

FIGS. 13 through 18 illustrate a laparoscopic suturing device in accordance with a third embodiment of the invention. FIG. 13 shows the suturing device to comprise a suturing needle 60 and a suturing thread retriever 62 slidably housed within protective sleeve 64. The suturing needle 60 is formed with a helically-shaped front-end portion 66 as in the other embodiments and is connected at its proximal end to a hollow rear-end portion 68 by way of transitional portion 67. The suturing thread retriever 62 is formed of a slender extended body 70 having at its distal end a hook 72 or other means for grasping a loop in the suturing thread as discussed below. The suturing thread retriever 62 slides axially through the hollow protective sleeve 64, while the suturing needle is secured within the sleeve and can be operated by manipulating the sleeve. As in the other disclosed embodiments, the protective sleeve 64 is designed to be inserted through a cannula.

The sleeve 64 is formed to have a barrel-shaped body 74 and a flange 76 at its proximal end for limiting movement of the sleeve within the cannula. The proximal end of the suturing thread retriever has a bent portion 78 for manipulating the retriever.

As seen in FIG. 14, a suturing thread 80 is threaded through the hollow rear-end portion 68 of the suturing needle, looped around a bridge 82 and then secured to the distal end of the rear-end portion by, for example, being pinched beneath a crimping bar 84. The suturing device is then ready to be used as described below.

As an alternative to applying stitches in a manner to close an incision as shown in FIGS. 10 through 12, the laparoscopic suturing device in accordance with third embodiment of the present invention can also readily apply stitches as shown in FIGS. 15 through 18. In these figures, a suturing thread is applied around the lip of the incision 81, or opening, to provide what is known as a purse-string suture. The purse-string suture is desirably used to reduce the size of the incision or opening.

Figure 15:
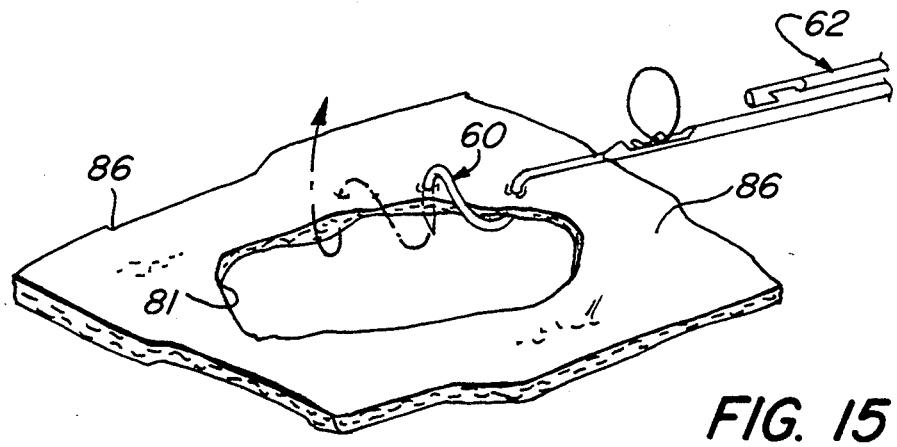
FIGS. 15 through 18 show a suturing operation using the laparoscopic suturing device of the third embodiment.
Figure 16:
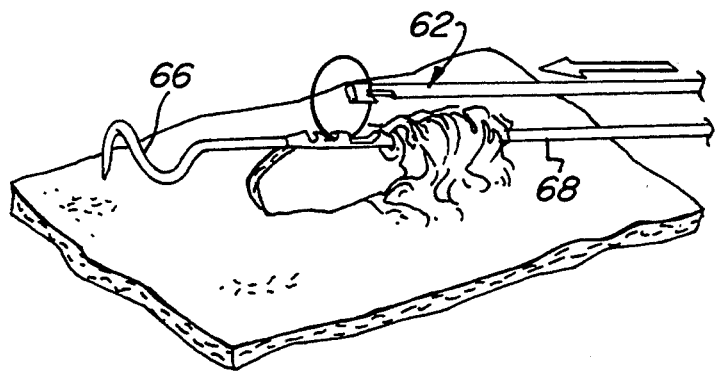
Figure 17:
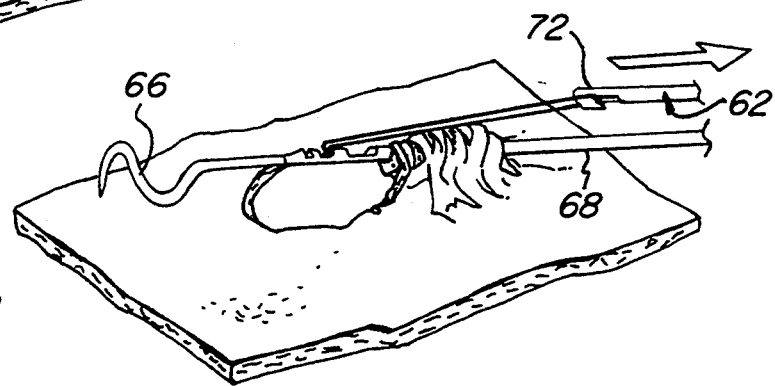
Figure 18:
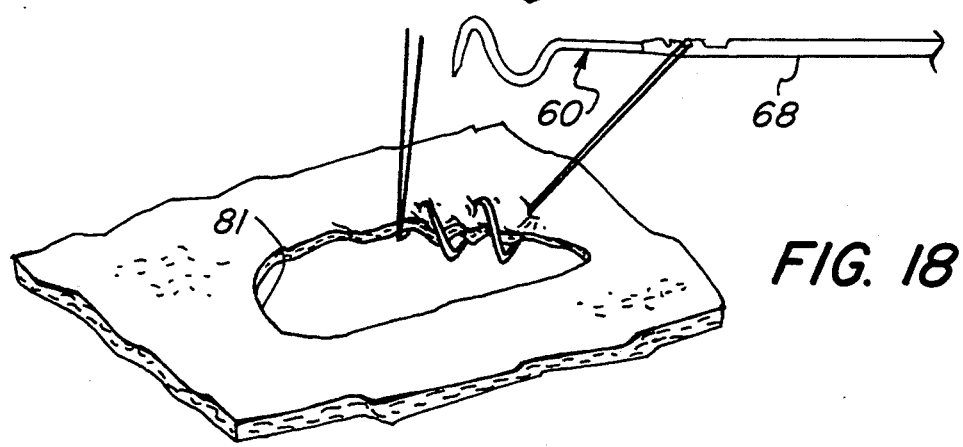

In FIG. 15 the suturing device is rotated about the axial center of the helical needle by manipulating the flange 76 to drive the helically-wound front-end portion into the tissue 86. The corkscrew-like motion of the front-end portion 66 drives the suturing needle through the tissue. When a desired number of holes are made in the tissue, a pair of forceps can be used to slide the tissue on the front-end rearwardly over the crimping bar 84 and the bridge 82 on the rear-end portion of the needle. The suturing thread retriever 62 is then used to grasp the loop 83 in the suturing thread 80. The suturing needle 60 is then withdrawn from the tissue as shown in FIG. 18 and removed from the cannula, followed by the suturing thread retriever. The looped end of the suturing thread and another end cut from the suturing thread are then knotted to form a double-threaded purse-string suture.

Figure 19:
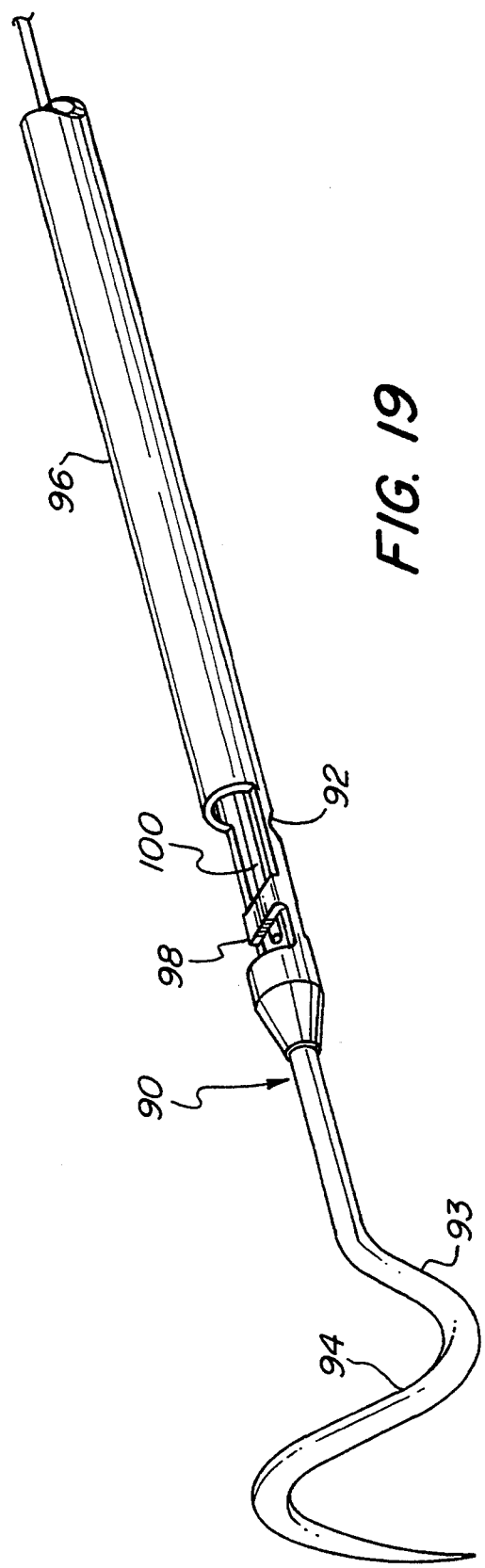
FIG. 19 is a perspective view of a laparoscopic suturing device in accordance with a fourth embodiment of the present invention.

The fourth embodiment of the present invention shown in FIG. 19 provides a suturing needle 90 that is similar to the suturing needle 60 described with reference to the third embodiment, but features a frangible notched section 92 on the suturing needle instead of a bridge. Thus, the suturing needle includes a helically-wound front-end portion 94 connected, by way of transitional portion 93, to a hollow rear-end portion 96. The rear-end portion includes a crimping bar 98, or other securing means, for securing one end of a suturing thread 100. The suturing needle 90 of the fourth embodiment is housed within a protected sleeve (not shown in FIG. 19) of the type disclosed in the third embodiment of the present invention.

In use, the suturing thread is stitched through the tissue in the same manner described above with respect to the third embodiment. The tissue is manipulated by forceps past the crimping bar 98 and the frangible notched section 92 in the rear-end portion 96 of the suturing needle. The forceps are then used to break or snap-off the suturing needle at the notched section. The broken-off portion of the suturing needle, which includes the front-end portion 94 and the section of the rear-end portion 96 having the crimping bar securing the end of the suturing thread, is withdrawn through the cannula, subsequent to withdrawing the remaining rear-end portion of the suturing needle. Two ends of the suturing thread are cut and tied to complete the suture.

Accordingly, the present invention provides a unique apparatus for applying sutures of various types in varied minimally-invasive surgical procedures. This apparatus can be easily and reliably used by skilled surgeons to enhance achievement of all of the benefits of such procedures.

Although specific embodiments of the present invention has been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A laparoscopic suturing device, comprising:
    a suturing needle formed with a helically-wound front-end portion having a sharp needle point at its distal end for penetrating tissue, a rear-end portion, a substantially straight middle portion connected to said rear-end portion, and a transitional portion connected between said middle portion and said helically-wound front-end portion, said middle portion extending along and aligned with a central axis of said helically-wound front-end portion; and
    a driver detachably connected to said rear-end portion, wherein
    said rear-end portion includes an offset section offset from an axial center of said suturing needle, with said offset section secured within said driver and capable of transmitting torsional and longitudinal force from said handle to said suturing needle.

2. A laparoscopic suturing device according to claim 1, said driver comprising an elongated shaft having a distal end connected to said rear-end portion of said surgical needle and a proximal end having handle means for manipulating said shaft.

3. A laparoscopic suturing device according to claim 2, wherein said driver is a hollow tubular shaft with a conically-shaped distal end for receiving said rear-end portion of said surgical needle.

4. A laparoscopic suturing device according to claim 1, further comprising a tubular sleeve for slidably receiving said driver and said suturing needle, said sleeve having a flange at its proximal end for limiting its axial movement within a cannula.

5. A laparoscopic suturing device according to claim 1, wherein said rear-end portion includes an axial opening at its proximal end for receiving a suturing thread to be secured thereto.

6. A laparoscopic suturing device according to claim 1, wherein said helically-wound front-end portion has at least a segment of one turn.

* * * * *